United States Patent
Swan et al.

(10) Patent No.: US 12,265,389 B2
(45) Date of Patent: *Apr. 1, 2025

(54) TECHNOLOGIES FOR PROVIDING A COGNITIVE CAPACITY TEST FOR AUTONOMOUS DRIVING

(71) Applicant: Mobileye Vision Technologies Ltd., Jerusalem (IL)

(72) Inventors: Johanna Swan, Scottsdale, AZ (US); Shahrnaz Azizi, Cupertino, CA (US); Rajashree Baskaran, Portland, OR (US); Melissa Ortiz, San Jose, CA (US); Fatema Adenwala, Hillsboro, OR (US); Mengjie Yu, Folsom, CA (US)

(73) Assignee: Mobileye Vision Technologies Ltd., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/860,741

(22) Filed: Jul. 8, 2022

(65) Prior Publication Data
US 2023/0029545 A1    Feb. 2, 2023

Related U.S. Application Data

(63) Continuation of application No. 16/234,032, filed on Dec. 27, 2018, now Pat. No. 11,422,551.

(51) Int. Cl.
*G05D 1/00* (2024.01)
*A61B 5/00* (2006.01)
(Continued)

(52) U.S. Cl.
CPC .......... *G05D 1/0061* (2013.01); *A61B 5/162* (2013.01); *A61B 5/18* (2013.01); *A61B 5/742* (2013.01);
(Continued)

(58) Field of Classification Search
CPC .................................................. G05D 1/0061
See application file for complete search history.

(56) References Cited

U.S. PATENT DOCUMENTS 6,304,187 B1 * 10/2001 Pirim ........................ B60R 1/12
340/576
8,738,523 B1 * 5/2014 Sanchez ................ G06Q 40/00
705/4
(Continued)

FOREIGN PATENT DOCUMENTS

CN      112519789 A  *  3/2021  ............ B60W 40/00
JP      2021/508863 A    3/2021

OTHER PUBLICATIONS

Chinese Pattent Pub. No. CN 212365194 U (Nov. 26, 2018).*
Google Machine Translation of Chinese Patent Pub. No. CN103434400BU (2013) (Year: 2013).*

*Primary Examiner* — Jean Paul Cass
(74) *Attorney, Agent, or Firm* — FINNEGAN, HENDERSON, FARABOW, GARRETT & DUNNER LLP (57) ABSTRACT

Technologies for providing a cognitive capacity test for autonomous driving include a compute device. The compute device includes circuitry that is configured to display content to a user, prompt a message to the user to turn user's attention to another activity that needs situational awareness, receive a user response, and analyze the user response to determine an accuracy of the user response and a response time, wherein the accuracy and response time are indicative of a cognitive capacity of the user to assume control of an autonomous vehicle when the autonomous vehicle encounters a situation that the vehicle is unable to navigate.

14 Claims, 5 Drawing Sheets

(51) Int. Cl.
    *A61B 5/16*     (2006.01)
    *A61B 5/18*     (2006.01)
    *A63F 13/25*    (2014.01)
    *A63F 13/44*    (2014.01)
    *A63F 13/803*   (2014.01)

(52) U.S. Cl.
    CPC ............ *A63F 13/44* (2014.09); *A63F 13/803* (2014.09); *A61B 5/0002* (2013.01); *A61B 5/4088* (2013.01); *A63F 13/25* (2014.09); *A63F 2300/30* (2013.01); *G05D 1/0088* (2013.01)

(56) References Cited

U.S. PATENT DOCUMENTS

| | | | |
|---|---|---|---|
| 10,611,384 B1* | 4/2020 | VandenBerg, III | B60W 40/08 |
| 11,644,834 B2 | 5/2023 | Ditty et al. | |
| 2005/0080565 A1* | 4/2005 | Olney | B60W 50/16 |
| | | | 340/903 |
| 2016/0046294 A1* | 2/2016 | Lee | G08B 21/06 |
| | | | 340/576 |
| 2018/0189581 A1* | 7/2018 | Turcot | G06V 20/597 |
| 2019/0176837 A1* | 6/2019 | Williams | G06V 20/593 |
| 2020/0101981 A1* | 4/2020 | Phillips | G07C 5/085 |

\* cited by examiner

TECHNOLOGIES FOR PROVIDING A COGNITIVE CAPACITY TEST FOR AUTONOMOUS DRIVING

CROSS REFERENCE TO RELATED APPLICATIONS

This application is a continuation (and claims the benefit of priority under 35 U.S.C. § 120) of U.S. application Ser. No. 16/234,032, filed Dec. 27, 2018 and entitled "TECHNOLOGIES FOR PROVIDING A COGNITIVE CAPACITY TEST FOR AUTONOMOUS DRIVING". The disclosure of the prior application is considered part of and is hereby incorporated by reference in its entirety in the disclosure of this application.

BACKGROUND

Automated driving may require a driver to alter a level of active engagement with a vehicle on short notice. Generally, an ability of a driver to re-contextualize from another activity to taking control of the vehicle may take significantly different amounts of time depending on the driver's skills, an amount of driving experience, and the level of autonomy provided by the vehicle.

For example, a vehicle with an autonomous driving feature may manage most aspects of driving in the right conditions but may prompt the driver to intervene when the vehicle encounters a scenario that the vehicle cannot navigate. In another example, a vehicle may operate without human input or oversight but only under select conditions defined by factors such as road type or geographic area. In other words, the driver may manage all driving duties on surface streets then become a passenger as the vehicle enters a highway. In both examples, the vehicle may be required to alert the driver to take control of the vehicle in certain situations.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 1:
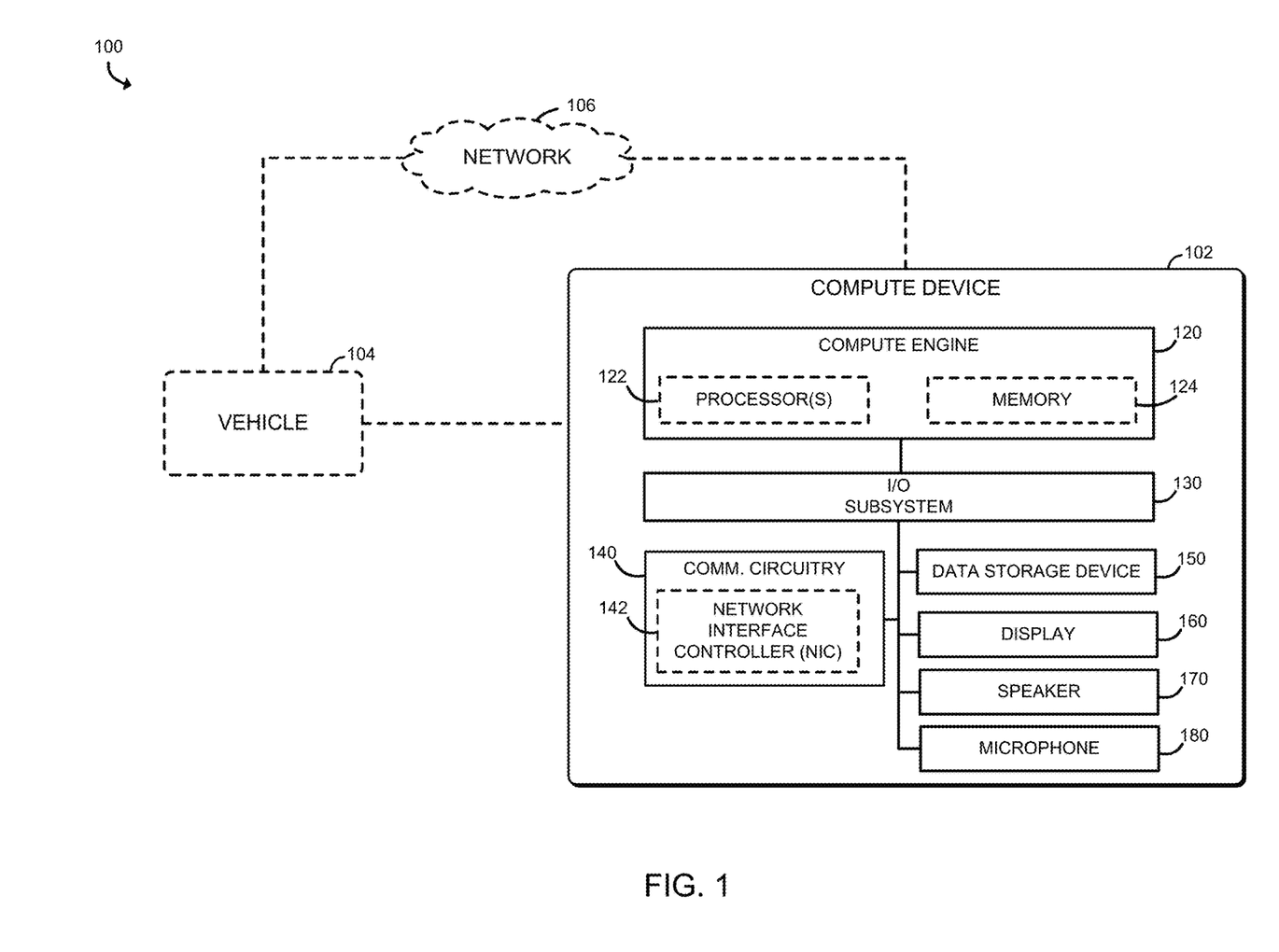
FIG. 1 is a simplified block diagram of at least one embodiment of an autonomous system that includes a compute device that may communicate with a vehicle.

Referring now to FIG. 1, an illustrative system 100 for determining a cognitive capacity level of a user is shown. The system 100 includes a compute device 102 that may communicate with a vehicle 104 that has autonomous driving features. The vehicle 104 may manage most aspects of driving in the right conditions but may prompt the driver to intervene when the vehicle 104 encounters a scenario it cannot navigate. As such, the vehicle 104 may require the driver or user of the vehicle to re-contextualize from a previous activity to take control of the vehicle 104. In use, the compute device 102 may provide a cognitive capacity test to a user to measure the cognitive context switching capacity of a user. A particular instantiation can be gamification of the test, for example, a game that immerses the user in a video and then asks to turn the user's attention to another activity that needs situational awareness. For example, the compute device 102 may ask the user to count specific objects in a complex visual pattern with distracting sounds. The speed and accuracy with which the user completes the cognitive capacity test may be translated to a level of cognitive capacity for context switching that will set the time needed for the vehicle 104 to warn the user before expecting the user to take control. As discussed further below, the cognitive capacity test may be not only used to determine whether the user is qualified to drive a vehicle with autonomous driving features (i.e., whether the user can re-contextualize from another activity to take control of the vehicle) but also to change features of the vehicle 104 based on the cognitive capacity test result of the user.

In the illustrative embodiment, the vehicle 104 is embodied as an automobile (e.g., car or truck). However, in other embodiments, the vehicle 104 may be embodied as any type of vehicle or machine capable of transporting an occupant including, but not limited to, a bus, a train, an airplane, a boat, a vehicle simulator, or any other machine, system, or environment that has autonomous driving features.

The system 100 may include a network 106 (e.g., connecting the compute device 102 to components of the vehicle 104), which may be embodied as any type of wired or wireless communication network, including controller area networks (CANs), local area networks (LANs) or wide area networks (WANs), global networks (e.g., the Internet), cellular networks (e.g., Global System for Mobile Communications (GSM), 3G, 4G, 5G, Long Term Evolution (LTE), Worldwide Interoperability for Microwave Access (WiMAX), etc.), digital subscriber line (DSL) networks, cable networks (e.g., coaxial networks, fiber networks, etc.), telephony networks, or any combination thereof. As such, the network 106 may include any number of additional devices, s computers, routers, and switches, to facilitate communications thereacross.

The compute device 102 may be embodied as any type of computation or computer device capable of playing media and performing the functions described herein, including, without limitation, a tablet computer, a smartphone, a laptop computer, a notebook, desktop computer, a netbook, an Ultrabook™, a smart device, a personal digital assistant, a mobile Internet device, a compute device mounted in the vehicle 104 (e.g., as an infotainment system), and/or other compute device. As shown in FIG. 1, the illustrative compute device 102 includes a compute engine (also referred to herein as "compute engine circuitry") 120, an input/output (I/O) subsystem 130, communication circuitry 140, one or more data storage devices 150, a display 160, a speaker 170, and a microphone 180. It should be appreciated that, in other embodiments, the compute device 102 may include other or additional components, such as those commonly found in a computer (e.g., a display, peripheral devices, etc.). Additionally, in some embodiments, one or more of the illustrative components may be incorporated in, or otherwise form a portion of, another component. The compute engine 120 may be embodied as any type of device or collection of devices capable of performing various compute functions described below. In some embodiments, the compute engine 120 may be embodied as a single device such as an integrated circuit, an embedded system, a field-programmable gate array (FPGA), a system-on-a-chip (SOC), or other integrated system or device. In the illustrative embodiment, the compute engine 120 includes or is embodied as a processor 122 and a memory 124. The processor 122 may be embodied as any type of processor capable of performing the functions described herein. For example, the processor 122 may be embodied as a multi-core processor(s), a microcontroller, or other processor or processing/controlling circuit. In some embodiments, the processor 122 may be embodied as, include, or be coupled to an FPGA, an application specific integrated circuit (ASIC), reconfigurable hardware or hardware circuitry, or other specialized hardware to facilitate performance of the functions described herein.

The main memory 124 may be embodied as any type of volatile (e.g., dynamic random access memory (DRAM), etc.) or non-volatile memory or data storage capable of performing the functions described herein. Volatile memory may be a storage medium that requires power to maintain the state of data stored by the medium. Non-limiting examples of volatile memory may include various types of random access memory (RAM), such as dynamic random access memory (DRAM) or static random access memory (SRAM). One particular type of DRAM that may be used in a memory module is synchronous dynamic random access memory (SDRAM). In particular embodiments, DRAM of a memory component may comply with a standard promulgated by JEDEC, such as JESD79F for DDR SDRAM, JESD79-2F for DDR2 SDRAM, JESD79-3F for DDR3 SDRAM, JESD79-4A for DDR4 SDRAM, JESD209 for Low Power DDR (LPDDR), JESD209-2 for LPDDR2, JESD209-3 for LPDDR3, and JESD209-4 for LPDDR4. Such standards (and similar standards) may be referred to as DDR-based standards and communication interfaces of the storage devices that implement such standards may be referred to as DDR-based interfaces.

In one embodiment, the memory device is a block addressable memory device, such as those based on NAND or NOR technologies. A memory device may also include a three dimensional crosspoint memory device (e.g., Intel 3D XPoint™ memory), or other byte addressable write-in-place nonvolatile memory devices. In one embodiment, the memory device may be or may include memory devices that use chalcogenide glass, multi-threshold level NAND flash memory, NOR flash memory, single or multi-level Phase Change Memory (PCM), a resistive memory, nanowire memory, ferroelectric transistor random access memory (FeTRAM), anti-ferroelectric memory, magnetoresistive random access memory (MRAM) memory that incorporates memristor technology, resistive memory including the metal oxide base, the oxygen vacancy base and the conductive bridge Random Access Memory (CB-RAM), or spin transfer torque (STT)-MRAM, a spintronic magnetic junction memory based device, a magnetic tunneling junction (MTJ) based device, a DW (Domain Wall) and SOT (Spin Orbit Transfer) based device, a thyristor based memory device, or a combination of any of the above, or other memory. The memory device may refer to the die itself and/or to a packaged memory product.

The compute engine 120 is communicatively coupled to other components of the compute device 102 via the I/O subsystem 130, which may be embodied as circuitry and/or components to facilitate input/output operations with the compute engine 120 (e.g., with the processor 122 and/or the main memory 124), the data storage device 150, the display 160, the speaker 170, the microphone 180, and other components of the compute device 102. For example, the I/O subsystem 130 may be embodied as, or otherwise include, memory controller hubs, input/output control hubs, integrated sensor hubs, firmware devices, communication links (e.g., point-to-point links, bus links, wires, cables, light guides, printed circuit board traces, etc.), and/or other components and subsystems to facilitate the input/output operations. In some embodiments, the I/O subsystem 130 may form a portion of a system-on-a-chip (SoC) and be incorporated, along with one or more of the processor 122, the main memory 124, and other components of the compute device 102, into the compute engine 120.

The communication circuitry 140 may be embodied as any communication circuit, device, or collection thereof, capable of enabling communications over a network (not shown) between the compute device 102 and another compute device. The communication circuitry 140 may be configured to use any one or more communication technology (e.g., wired or wireless communications) and associated protocols (e.g., Ethernet, Bluetooth®, Wi-Fi®, WiMAX, etc.) to effect such communication.

The illustrative communication circuitry 140 includes a network interface controller (NIC) 142. The NIC 142 may be embodied as one or more add-in-boards, daughter cards, network interface cards, controller chips, chipsets, or other devices that may be used by the compute device 102 to connect with another compute device. In some embodiments, the NIC 142 may be embodied as part of a system-on-a-chip (SoC) that includes one or more processors, or included on a multichip package that also contains one or more processors. In some embodiments, the NIC 142 may include a local processor (not shown) and/or a local memory (not shown) that are both local to the NIC 142. In such embodiments, the local processor of the NIC 142 may be capable of performing one or more of the functions of the compute engine 120 described herein. Additionally or alternatively, in such embodiments, the local memory of the NIC 142 may be integrated into one or more components of the compute device 102 at the board level, socket level, chip level, and/or other levels.

The compute device 102 may include one or more data storage devices 150. In the illustrative embodiment, the data storage device 150 may be embodied as any type of device configured for short-term or long-term storage of data such as, for example, memory devices and circuits, memory cards, hard disk drives, solid-state drives, or other data storage device. The data storage device 150 may include a system partition that stores data and firmware code for the data storage device 150 and configuration data for features of the data storage device 150. The data storage device 150 may also include one or more operating system partitions that store data files and executables for operating systems. In some embodiments, the data storage device 150 may store one or more cognitive capacity tests.

The display 160 may be embodied as any type of display capable of displaying digital information such as a liquid crystal display (LCD), a light emitting diode (LED), a plasma display, a cathode ray tube (CRT), or other type of display device. The display 160 may include a touch screen to allow user interaction during a cognitive capacity test. It should be appreciated that the display 160 may be embodied as a part of the compute device 102 or may be positioned external to the compute device 102. For example, if the compute device 102 is embodied as a mobile device, content (e.g., video) is displayed on a screen of the mobile device. In some embodiments, if the compute device 102 can communicate with a vehicle, the compute device 102 may display the content on a graphical user interface unit of the vehicle 104. The content may be any multimedia content that occupies a user's attention.

Figure 2:
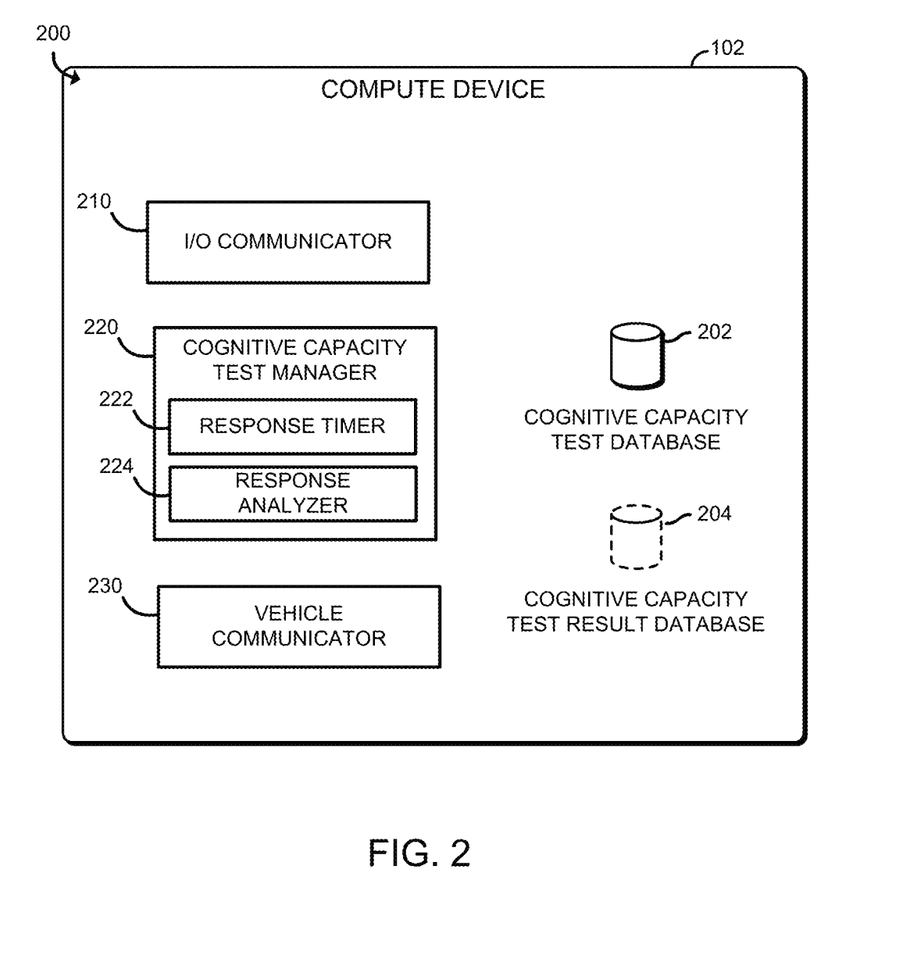
FIG. 2 is a simplified block diagram of at least one embodiment of the compute device of FIG. 1.

Referring now to FIG. 2, in use, the compute device 102 establishes an environment 200. The illustrative environment 200 includes a cognitive capacity test database 202 that stores one or more cognitive capacity tests. In some embodiments, the illustrative environment 200 may include a cognitive capacity test result database that stores test results of a user (e.g., a cognitive capacity test identifier indicating which test a user has taken, a user response, a response time, and accuracy of the response). The illustrative environment 200 further includes an input/output (I/O) communicator 210, a cognitive capacity test manager 220, and a vehicle communicator 230. The cognitive capacity test manager 220 further includes a response timer 222 and a response analyzer 224. The various components of the environment 200 may be embodied as hardware, firmware, software, or a combination thereof. As such, in some embodiments, one or more of the components of the environment 200 may be embodied as circuitry or collection of electrical devices (e.g., an I/O communicator circuit 210, a cognitive capacity test manager circuit 220, a response timer circuit 222, a response analyzer circuit 224, a vehicle communicator circuit 230, etc.). It should be appreciated that, in such embodiments, one or more of the I/O communicator circuit 210, the cognitive capacity test manager circuit 220, the response timer circuit 222, the response analyzer circuit 224, and/or the vehicle communicator circuit 230 may form a portion of one or more of the compute engine 120, the I/O subsystem 130, the communication subsystem 140, and/or other components of the compute device 102. Additionally, in some embodiments, one or more of the illustrative components of the environment 200 may form a portion of another component and/or one or more of the illustrative components may be independent of one another. Further, in some embodiments, one or more of the components of the environment 200 may be embodied as virtualized hardware components or emulated architecture, which may be established and maintained by the compute engine 120 or other components of the compute device.

The input/output (I/O) communicator 210 is configured to facilitate communication between the cognitive capacity test manager 220 and the input and output devices (e.g., the display 160, the speaker 170, and the microphone 180) of the compute device 102. The I/O communicator 210 outputs a cognitive capacity test on the display 160 to a user and guides the user during the cognitive capacity test via the speaker 170. Subsequently, the I/O communicator 210 receives a response from the user via the microphone 180. In some embodiments, the I/O communicator 210 may receive the user response via the touch screen display 160.

The cognitive capacity test manager 220 is configured to manage a cognitive capacity test provided to a user. For example, the cognitive capacity test manager 220 transmits content (e.g., a video or a game) to the display 160 to be played to the user. For example, the cognitive capacity test manager 220 may send a complex visual pattern to be displayed to the user via the display 160 and distracting sounds to be played via the speaker 170. Subsequently, the cognitive capacity test manager 220 may send a message to the user to count specific objects in the complex visual pattern via the speaker 170 and receive a response from the user via the microphone 180 or the display 160, if the display 160 is a touch screen.

As discussed above, the cognitive capacity test manager 220 further includes the response timer 222 and the response analyzer 224. The response timer 222 is configured to determine a response time of the user and further determine whether the response time is within a predefined acceptable range. The cognitive capacity test manager 220 may determine that the user passed the cognitive capacity test if the user response time is within the predefined acceptable range and failed the cognitive capacity test if the user response time is not within the predefined acceptable range. The response analyzer 224 is configured to determine whether the user response is correct. Again, the cognitive capacity test manager 220 may determine that the user passed the cognitive capacity test if the user response is correct and failed the cognitive capacity test if the user response is not correct.

The vehicle communicator 230 is configured to facilitate communication between the compute device 102 and the vehicle 104. The vehicle communicator 230 may be configured to communicate with the vehicle 104 to unlock the vehicle 104 if the user is qualified (i.e., passed the cognitive capacity test) to drive the vehicle 104 with the autonomous driving features. If, however, the user is not qualified, the vehicle communicator 230 may communicate with the vehicle 104 to update a system cognitive capacity level of the vehicle 104 as a function of the user's cognitive capacity test result. For example, the vehicle communicator 230 may send a message to the vehicle 104 to adjust a warning time as a function of the user's cognitive capacity test result. As discussed above, the vehicle 104 with the autonomous driving features warns, notifies, or prompts the user of the vehicle 104 to intervene when the vehicle 104 detects an upcoming scenario that it cannot navigate. The warning time is a time period that the vehicle 104 warns the user in advance of encountering the scenario to allow the user to prepare to take control of the vehicle 104. In the illustrative embodiment, the vehicle communicator 230 may communicate with the vehicle to adjust the warning time based on the accuracy of the user response and/or the response time the user.

For example, if the user's response was not accurate, the vehicle communicator 230 may communicate with the vehicle 104 to set the maximum warning time in an effort to provide the user enough time to re-contextualize from another activity to take control of the vehicle 104. In order to do that, the vehicle 104 may prompt the user while the vehicle 104 is still determining whether it requires a user intervention. In other words, when the vehicle 104 encounters a scenario, the vehicle 104 may prompt the user to gain user's attention while it determines whether the user intervention is required, such that the user is alert and ready to take the driving duties if the vehicle 104 determines that it cannot navigate under the scenario. If the user's response was accurate but the response time was outside of the predefined acceptable range, the vehicle communicator 230 may communicate with the vehicle 104 to update the warning time using an algorithm. For example, every five second incremental delay in the response time may add three seconds to the warning time. In some embodiments, the algorithm may include other variables, such as gender, age, disability, eyesight, or general health condition of the user.

Figure 3:
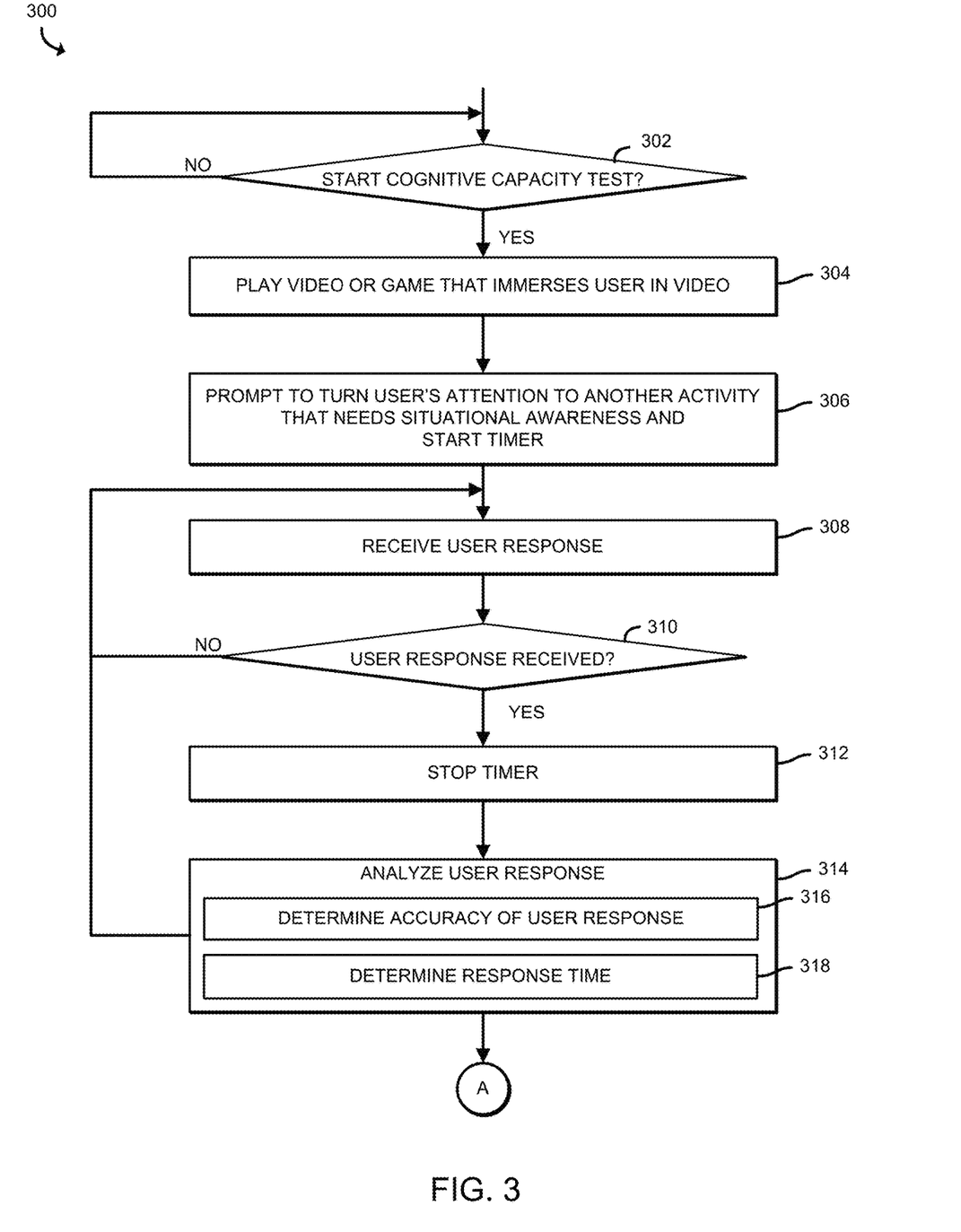
FIGS. 3-5 are a simplified flow diagram of at least one embodiment of a method for determining a cognitive capacity level of a user that may be executed by the compute device of FIGS. 1 and 2.
Figure 4:
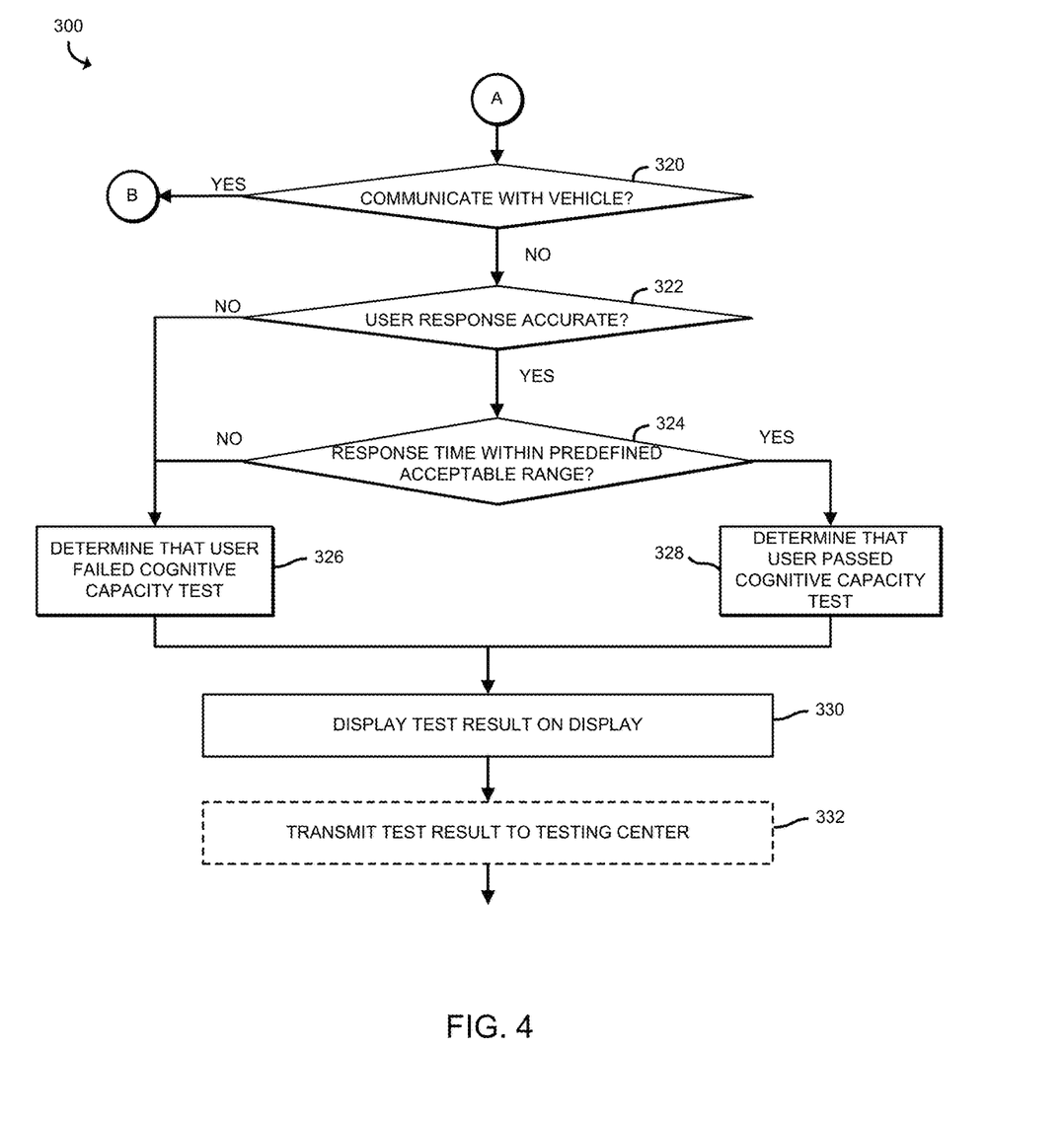
Figure 5:
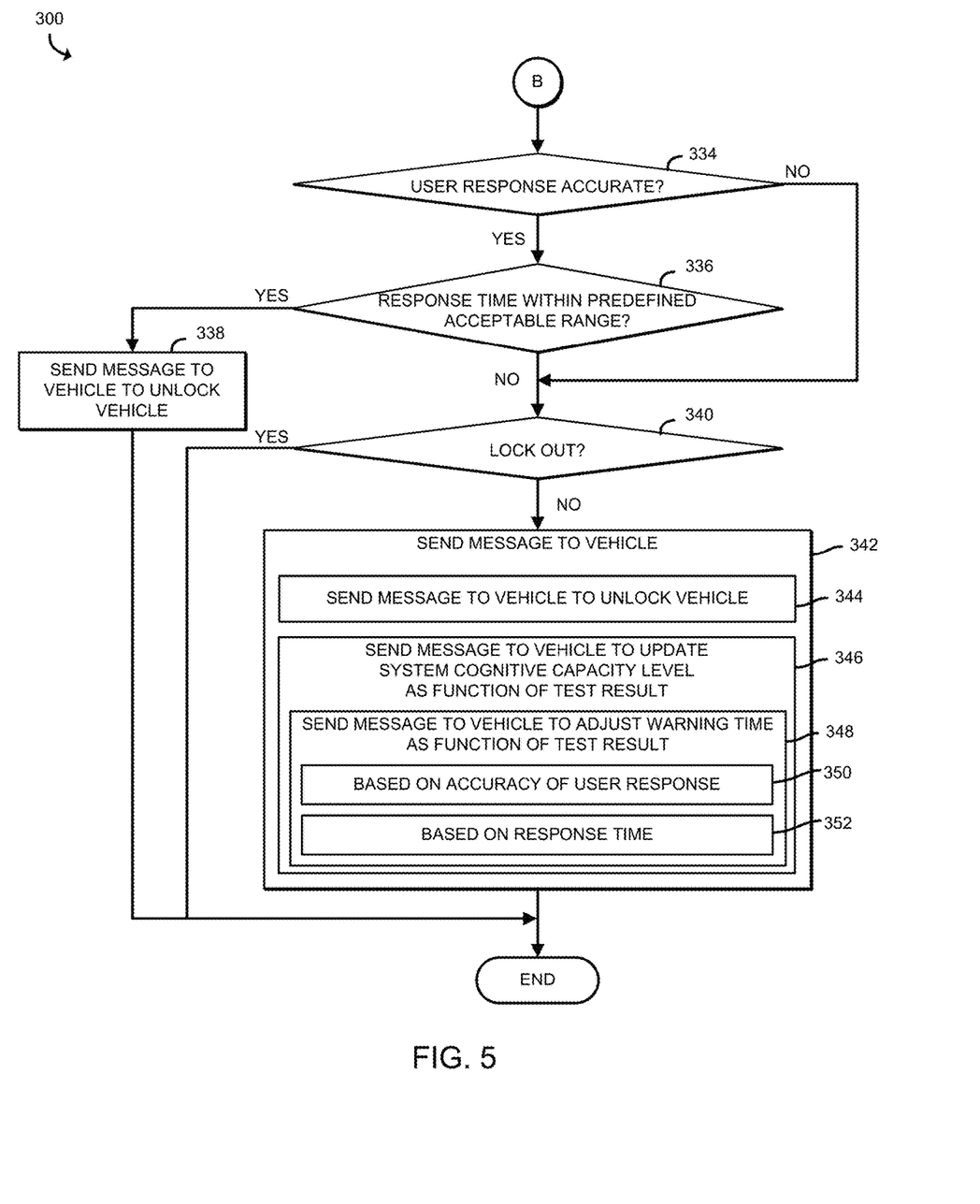

Referring now to FIGS. 3-5, in use, the compute device 102 may execute a method 300 for determining a cognitive capacity level of a user. As discussed further below, a cognitive capacity test may be used to determine whether the user is qualified to drive a vehicle with autonomous driving features (i.e., whether the user can re-contextualize from another activity to take control of the vehicle) and, in some embodiments, change features of the vehicle 104 based on the cognitive capacity test result of the user. To do so, the method 300 begins with block 302 in which the compute device 102 determines to start a cognitive capacity test. The compute device 102 may determine to start a cognitive capacity test in response to a request (e.g., a request by the user to be tested, a request by the user to drive the vehicle, etc.) and/or based on other factors. Regardless, if the compute device 102 determines to start the cognitive capacity test, the method 300 advances to block 304. If, however, the compute device 102 determines not to start the cognitive capacity test, the method 300 loops back to block 302 to continue determining whether to start the cognitive capacity test.

In block 304, the compute device 102 plays a video or a game on a display 160 that immerses user in the video. It should be appreciated that the display 160 may be embodied as a part of the compute device 102 or may be positioned external to the compute device 102. For example, if the compute device 102 is embodied as a mobile device, the video is displayed on a screen of the mobile device. In another example, if the compute device 102 can communicate with the vehicle 104, the compute device 102 may display the video on a graphic user interface unit of the vehicle 104.

In block 306, the compute device 102 prompts to turn user's attention to another activity that needs situational awareness while the video or game is displayed. For example, the compute device 102 may display a complex visual pattern with distracting sounds and ask the user to count specific objects in the complex visual pattern. Simultaneously, in the illustrative embodiment, the compute device 102 starts a timer. Subsequently, in block 308, the compute device 102 may receive a user response.

If the compute device 102 determines that the user response was not received in block 310, the method 300 loops back to block 308 to continue monitoring for a user response. If, however, the compute device 102 determines that the user response was received in block 310, the method 300 advances to block 312. In response to receiving the user response, the compute device 102 stops the timer as illustrated in block 312.

In block 314, the compute device 102 analyzes the user response. To do so, the compute device 102 determines an accuracy of the user response, as illustrated in block 316. The compute device 102 further determines a response time. The response time is represented by an amount of time that has elapsed according to the timer. Subsequently, the method 300 advances to block 320 in FIG. 4.

In block 320, the compute device 102 determines whether the compute device 102 is configured to communicate with a vehicle 104. If not, the method 300 advances to block 322. For example, as discussed above, the cognitive capacity test may be conducted to determine whether the user is qualified to obtain a driver's license for a vehicle with the autonomous driving features. Alternatively, the user may take the cognitive to capacity test to practice and prepare for the driver's license test. In such examples, the compute device 102 might not be configured to communicate with the vehicle 104.

In block 322, the compute device 102 determines the subsequent course of action based on whether the user response is accurate (e.g., as determined in block 316 of FIG. 3). If the compute device 102 determined that the user response is not accurate, the method 300 skips ahead to block 326 to determine that the user failed cognitive capacity test. If, however, the compute device 102 determined that the user response is accurate, the method 300 advances to block 324 to determine whether the response time is within a predefined acceptable range.

If the compute device 102 determines that the response time is not within the predefined acceptable range, the method 300 advances to block 326 to determine that the user failed cognitive capacity test. If, however, the compute device 102 determines that the user response is within the predefined acceptable range, the method 300 advances to block 328 to determine that the user passed cognitive capacity test.

Subsequently, in the illustrative embodiment, the cognitive capacity test result is displayed on the display 160 as illustrated in block 330. In some embodiments, where the cognitive capacity test is being provided for the driver's license qualification test, the compute device 102 may transmit the cognitive capacity test result to a testing center, as indicated in block 332.

Referring back to block 320, if the compute device 102 determines that the compute device 102 is not configured to communicate with the vehicle 104 in block 320, the method 300 skips ahead to block 334 of FIG. 5. In block 334, the compute device 102 determines a subsequent course of action based on whether the user response is accurate. If the user response is not accurate, the method 300 skips ahead to block 340. If, however, the user response is accurate, the method 300 advances to block 336 to determine whether the response time is within a predefined acceptable range. If the compute device 102 determines that the user response is within the predefined acceptable range, the method 300 advances to block 338 to send a message to the vehicle 104 to unlock the vehicle 104. If, however, the compute device 102 determines that the response time is not within the predefined acceptable range, the method 300 advances to block 340.

In block 340, the compute device 102 communicates with the vehicle 104 to determine whether the vehicle 104 permits the user to be locked out of the vehicle 104. For example, a manufacture setting of the vehicle 104 may not allow an unqualified user (i.e., a user who fails the cognitive capacity test) to gain access to the vehicle 104 that has autonomous driving features for safety of the user and other drivers or passengers on the road. If the compute device 102 determines that the vehicle 104 allows the unqualified user to be locked out, the method 300 ends (e.g., the vehicle remains locked and the user is unable to operate the vehicle 104).

If, however, the compute device 102 determines that the vehicle 104 does not allow the lock out, the method 300 advances to block 342 to send a message to the vehicle 104. For example, the compute device 102 sends a message to the vehicle 104 to unlock the vehicle 104 as indicated in block 344. Additionally, the compute device 102 sends a message to the vehicle 104 to update a system cognitive capacity level as a function of the cognitive capacity test result of the user, as indicated in block 346. To do so, in block 348, the device 102 sends a message to the vehicle 104 to adjust a warning time as a function of the cognitive capacity test result of the user. As discussed above, the vehicle 104 with the autonomous driving features may warn, notify, or prompt the user of the vehicle 104 to intervene when it encounters a scenario that it cannot navigate. The warning time may be adjusted based on the accuracy of the user response and/or the response time of the user as illustrated in blocks 350 and 352.

For example, if the user's response was not accurate, the compute device 102 may communicate with the vehicle 104 to set the maximum warning time in effort to provide the user enough time to re-contextualize from another activity to take control of the vehicle 104. In order to do that, the vehicle 104 may prompt the user while the vehicle 104 is still determining whether it requires user intervention. In other words, when the vehicle 104 encounters a scenario, the vehicle 104 may prompt the user to gain user's attention while the vehicle 104 determines whether the user intervention is actually required, such that the user is alert and ready to take the driving duties if the vehicle 104 determines that it cannot navigate under the scenario.

If the user's response was accurate but the response time was outside of the predefined acceptable range, the vehicle 104 may update the warning time using an algorithm. For example, every five second incremental delay in the response time may add three seconds to the warning time. In some embodiments, the algorithm may include other variables, such as gender, age, disability, eyesight, or general health condition of the user.

EXAMPLES

Illustrative examples of the technologies disclosed herein are provided below. An embodiment of the technologies may include any one or more, and any combination of, the examples described below.

Example 1 includes a compute device comprising circuitry configured to display content to a user; prompt a message to the user to turn user's attention to another activity that needs situational awareness; receive a user response; and analyze the user response to determine an accuracy of the user response and a response time, wherein the accuracy and response time are indicative of a cognitive capacity of the user to assume control of an autonomous vehicle when the autonomous vehicle encounters a situation that the vehicle is unable to navigate.

Example 2 includes the subject matter of Example 1, and wherein the content is a video game.

Example 3 includes the subject matter of any of Examples 1 and 2, and wherein the circuitry is further configured to start a timer in response to a prompt of the message to the user; and stop the timer, in response to a receipt of the user response.

Example 4 includes the subject matter of any of Examples 1-3, and wherein to analyze the user response to determine the response time comprises to determine the response time based on the timer and determine whether the response time is within a predefined acceptable range.

Example 5 includes the subject matter of any of Examples 1-4, and wherein the circuitry is further configured to determine whether to communicate with an vehicle with autonomous driving features; and send, in response to a determination that the compute device is to communicate with the vehicle, a message to the vehicle to unlock the vehicle.

Example 6 includes the subject matter of any of Examples 1-5, and wherein to send the message to the vehicle to unlock the vehicle comprises to send, in response to a determination that the user response is accurate, the message to the vehicle to unlock the vehicle.

Example 7 includes the subject matter of any of Examples 1-6, and wherein to send the message to the vehicle to unlock the vehicle comprises to send, in response to a determination that the response time is within the predefined acceptable range, the message to the vehicle to unlock the vehicle.

Example 8 includes the subject matter of any of Examples 1-7, and wherein the circuitry is further configured to determine whether to communicate with an vehicle with autonomous driving features; and send, in response to a determination that the compute device is to communicate with the vehicle, a message to the vehicle to adjust a warning time as a function of a cognitive capacity test result of the user.

Example 9 includes the subject matter of any of Examples 1-8, and wherein the circuitry is further configured to determine, whether to communicate with an vehicle with autonomous driving features; and determine, in response to a determination that the compute device is not to communicate with the vehicle, whether the user passed or fail the cognitive capacity test.

Example 10 includes the subject matter of any of Examples 1-9, and wherein the circuitry is further configured to send a result of the analysis to a testing center.

Example 11 includes one or more machine-readable storage media comprising a plurality of instructions stored thereon that, in response to being executed, cause a compute device to display content to a user; prompt a message to the user to turn user's attention to another activity that needs situational awareness; receive a user response; and analyze the user response to determine an accuracy of the user response and a response time, wherein the accuracy and response time are indicative of a cognitive capacity of the user to assume control of an autonomous vehicle when the autonomous vehicle encounters a situation that the vehicle is unable to navigate.

Example 12 includes the subject matter of Example 11, and further including a plurality of instructions that in response to being executed cause the compute device to start a timer in response to a prompt of the message to the user; and stop the timer, in response to a receipt of the user response; wherein to analyze the user response to determine the response time comprises to determine the response time based on the timer and determine whether the response time is within a predefined acceptable range.

Example 13 includes the subject matter of any of Examples 11 and 12, and further including a plurality of instructions that in response to being executed cause the compute device to determine whether to communicate with an vehicle with autonomous driving features; and send, in response to a determination that the compute device is to communicate with the vehicle, a message to the vehicle to unlock the vehicle.

Example 14 includes the subject matter of any of Examples 11-13, and wherein to send the message to the vehicle to unlock the vehicle comprises to send, in response to a determination that the user response is accurate, the message to the vehicle to unlock the vehicle.

Example 15 includes the subject matter of any of Examples 11-14, and wherein to send the message to the vehicle to unlock the vehicle comprises to send, in response to a determination that the response time is within the predefined acceptable range, the message to the vehicle to unlock the vehicle.

Example 16 includes the subject matter of any of Examples 11-15, and further including a plurality of instructions that in response to being executed cause the compute device to determine whether to communicate with an vehicle with autonomous driving features; and send, in response to a determination that the compute device is to communicate with the vehicle, a message to the vehicle to adjust a warning time as a function of a cognitive capacity test result of the user.

Example 17 includes the subject matter of any of Examples 11-16, and further including a plurality of instructions that in response to being executed cause the compute device to determine, whether to communicate with an vehicle with autonomous driving features; and determine, in response to a determination that the compute device is not to communicate with the vehicle, whether the user passed or fail the cognitive capacity test.

Example 18 includes the subject matter of any of Examples 11-17, and wherein the circuitry is further configured to send a result of the analysis to a testing center.

Example 19 includes a method comprising displaying, by a compute device, content to a user, prompting, by the compute device, a message to the user to turn user's attention to another activity that needs situational awareness; receiving, by the compute device, a user response; and analyzing, by the compute device, the user response to determine an accuracy of the user response and a response time, wherein the accuracy and response time are indicative of a cognitive capacity of the user to assume control of an autonomous vehicle when the autonomous vehicle encounters a situation that the vehicle is unable to navigate.

Example 20 includes the subject matter of Example 19, and further including starting, by the compute device, a timer in response to prompting the message to the user; and stopping, by the compute device, the timer, in response to receiving the user response; wherein analyzing the user response to determine the response time comprises determining, by the compute device, the response time based on the timer and determining whether the response time is within a predefined acceptable range.

Example 21 includes the subject matter of any of Examples 19 and 20, and further including determining, by the compute device, whether to communicate with an vehicle with autonomous driving features and sending, by the compute device and in response to determining that the compute device is to communicate with the vehicle, a message to the vehicle to unlock the vehicle.

Example 22 includes the subject matter of any of Examples 19-21, and wherein sending the message to the vehicle to unlock the vehicle comprises sending, in response to determining that the user response is accurate and by the compute device, the message to the vehicle to unlock the vehicle.

Example 23 includes the subject matter of any of Examples 19-22, and wherein sending the message to the vehicle to unlock the vehicle comprises sending, in response to determining that the response time is within the predefined acceptable range, the message to the vehicle to unlock the vehicle.

Example 24 includes the subject matter of any of Examples 19-23, and further including determining, by the compute device, whether to communicate with an vehicle with autonomous driving features and sending, by the compute device and in response to determining that the compute device is to communicate with the vehicle, a message to the vehicle to adjust a warning time as a function of a cognitive capacity test result of the user.

Example 25 includes the subject matter of any of Examples 19-24, and further including determining, by the compute device, whether to communicate with an vehicle with autonomous driving features and determining, by the compute device and in response to determining that the compute device is not to communicate with the vehicle, whether the user passed or fail the cognitive capacity test.

The invention claimed is:

1. A compute device, comprising:
   circuitry configured to:
   transmit content to be displayed on a display device, the content to include a first activity to engage a user via the display device, wherein:
   the content is a video or a game; and
   the display device is a graphical user interface unit of an autonomous vehicle;
   prompt a message to the user, the message to require a response from the user;
   receive a user response to the message;
   analyze the user response to determine an accuracy of the user response and a response time of the user response, wherein the accuracy and response time are indicative of a cognitive capacity of the user to assume control of the autonomous vehicle when the autonomous vehicle encounters a situation that the autonomous vehicle is unable to navigate; and determining that the response time is outside a predefined acceptable range and preventing the autonomous vehicle from being unlocked such that the user is unable to operate the autonomous vehicle.

2. The compute device of claim 1, wherein the circuitry is further configured to:

start a timer in response to prompting of the message to the user; and stop the timer, in response to a receipt of the user response.

3. The compute device of claim 2, wherein to analyze the user response to determine the response time is to further include:

determining the response time based on the timer; and determining whether the response time is outside the predefined acceptable range.

4. The compute device of claim 1, wherein the circuitry is further configured to:

determine whether the autonomous vehicle permits the user to be prevented from gaining access to the autonomous vehicle.

5. The compute device of claim 4, wherein a determination that the autonomous vehicle permits the user to be prevented from gaining access to the autonomous vehicle is based, at least in part, on a manufacturer setting of the autonomous vehicle.

6. The compute device of claim 1, wherein the circuitry is further configured to:

determine whether the compute device is configured to communicate with the autonomous vehicle; and allow the autonomous vehicle to remain locked based, in part, on a determination that the compute device is to communicate with the autonomous vehicle.

7. The compute device of claim 1, wherein the circuitry is further configured to send a result of an analysis of the user response to a testing center.

8. One or more non-transitory machine-readable storage media comprising instructions stored thereon that, in response to being executed, cause a compute device to:

transmit content to be displayed on a display device, the content to include a first activity to engage a user via the display device, wherein:
the content is a video or a game; and
the display device is a graphical user interface unit of an autonomous vehicle;

prompt a message to the user, the message to require a response from the user;

receive a user response to the message;

analyze the user response to determine an accuracy of the user response and a response time of the user response, wherein the accuracy and response time are indicative of a cognitive capacity of the user to assume control of the autonomous vehicle with autonomous driving features when the autonomous vehicle encounters a situation that the autonomous vehicle is unable to navigate; and determining that the user response is not accurate and preventing the autonomous vehicle from being unlocked such that the user is unable to operate the autonomous vehicle.

9. The one or more non-transitory machine-readable storage media of claim 8, wherein the instructions, in response to being executed, cause the compute device further to:

start a timer in response to prompting the message to the user; and stop the timer, in response to a receipt of the user response.

10. The one or more non-transitory machine-readable storage media of claim 9, wherein the instructions, in response to being executed, cause the compute device further to:

determine the response time based on the timer; and determine whether the response time is outside a predefined acceptable range.

11. The one or more non-transitory machine-readable storage media of claim 8, wherein the instructions, in response to being executed, cause the compute device further to:

determine whether the autonomous vehicle permits the user to be prevented from gaining access to the autonomous vehicle.

12. The one or more non-transitory machine-readable storage media of claim 8, wherein the instructions, in response to being executed, cause the compute device further to:

determine whether the compute device is configured to communicate with the autonomous vehicle; and allow the autonomous vehicle to remain locked based, in part, on a determination that the compute device is to communicate with the autonomous vehicle.

13. A method, comprising:

providing, by a compute device, a content for display on a display device, wherein the content includes a first activity to engage a user via the display device, wherein:
the content is a video or a game; and
the display device is a graphical user interface unit of an autonomous vehicle;

prompting, by the compute device, a message to the user;

receiving, by the compute device, a user response to the message;

analyzing, by the compute device, the user response to determine an accuracy of the user response and a response time of the user response, wherein the accuracy and response time are indicative of a cognitive capacity of the user to assume control of the autonomous vehicle when the autonomous vehicle encounters a situation that the autonomous vehicle is unable to navigate; and determining that the response time is outside a predefined acceptable range and allowing the autonomous vehicle to remain locked to prevent the user from gaining access to the autonomous vehicle with autonomous driving features such that the user is unable to operate the autonomous vehicle.

14. The method of claim 13, further comprising:

starting a timer in response to the prompting the message to the user; and stopping the timer in response to receiving the user response, wherein the analyzing the user response to determine the response time comprises determining the response time based on the timer.

* * * * *